US011138489B2

(12) United States Patent
Takano

(10) Patent No.: US 11,138,489 B2
(45) Date of Patent: Oct. 5, 2021

(54) ENDOSCOPE AND WATERPROOF CAP OF ENDOSCOPE

(71) Applicant: OLYMPUS CORPORATION, Tokyo (JP)

(72) Inventor: Yuji Takano, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/158,125

(22) Filed: Jan. 26, 2021

(65) Prior Publication Data

US 2021/0150301 A1 May 20, 2021

Related U.S. Application Data

(63) Continuation of application No. PCT/JP2019/028065, filed on Jul. 17, 2019.

(30) Foreign Application Priority Data

Jul. 31, 2018 (JP) .............................. JP2018-144176

(51) Int. Cl.
*G06K 19/077* (2006.01)
*A61B 1/00* (2006.01)
*A61B 8/12* (2006.01)

(52) U.S. Cl.
CPC .... G06K 19/07758 (2013.01); A61B 1/00137 (2013.01); *A61B 8/12* (2013.01)

(58) Field of Classification Search
CPC ...................... G06K 19/07758; A61B 1/00137

(Continued)

(56) References Cited

U.S. PATENT DOCUMENTS 6,491,625 B1   12/2002  Newton et al.
2004/0231772 A1* 11/2004  Leonard ............ A61B 1/00062
                                                              150/161

(Continued)

FOREIGN PATENT DOCUMENTS

JP    2002-238847 A    8/2002
JP    2002-301028 A    10/2002
WO    2012/026176 A1    3/2012

OTHER PUBLICATIONS

International Search Report dated Oct. 21, 2019 issued in PCT/JP2019/028065.

*Primary Examiner* — Allyson N Trail
(74) *Attorney, Agent, or Firm* — Scully, Scott, Murphy & Presser, P.C.

(57) ABSTRACT

An endoscope includes: a connector to which a waterproof cap is detachably attachable; an RFID tag that is arranged in the connector; an RFID tag storing member that has an opening and is made of a conductive material, the RFID tag storing member being configured to store the RFID tag; an opening and closing member that is made of a conductive material shielding a radio wave, the opening and closing member being configured to open or close the opening; and a moving mechanism configured to move the opening and closing member to a position of releasing shielding of the radio wave in conjunction with attachment of the waterproof cap to the connector, and move the opening and closing member to a position of shielding the radio wave in conjunction with detachment of the waterproof cap from the connector.

8 Claims, 13 Drawing Sheets

(58) Field of Classification Search
USPC .......................................................... 235/492
See application file for complete search history.

(56) References Cited

U.S. PATENT DOCUMENTS

| | | | | |
|---|---|---|---|---|
| 2010/0004772 | A1* | 1/2010 | Elfstrom | G06Q 10/06 |
| | | | | 700/103 |
| 2010/0112815 | A1* | 5/2010 | O'Dougherty | B67D 7/34 |
| | | | | 438/689 |
| 2012/0035425 | A1* | 2/2012 | Schaller | B29C 45/14598 |
| | | | | 600/249 |
| 2013/0338503 | A1* | 12/2013 | Cohen | A61B 8/4411 |
| | | | | 600/443 |
| 2020/0330181 | A1* | 10/2020 | Junger | A61F 9/008 |
| 2021/0212796 | A1* | 7/2021 | Crotti | A61L 2/18 |

* cited by examiner

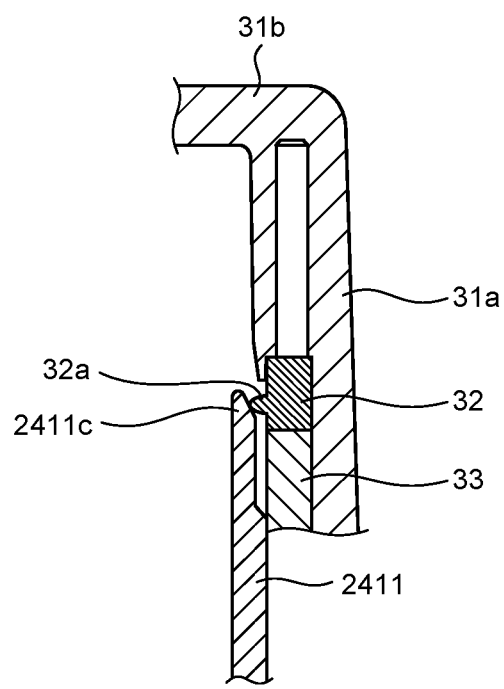

ENDOSCOPE AND WATERPROOF CAP OF ENDOSCOPE

CROSS-REFERENCE TO RELATED APPLICATIONS

This application is a continuation of PCT international application No. PCT/JP2019/028065 filed on Jul. 17, 2019, which designates the United States, incorporated herein by reference, and which claims the benefit of priority from Japanese Patent Application No. 2018-144176, filed on Jul. 31, 2018, incorporated herein by reference.

BACKGROUND

1. Technical Field

The present disclosure relates to an endoscope and a waterproof cap of an endoscope.

2. Related Art

In the relater art, WO 2012/026176 A discloses an endoscope in which a radio frequency identifier (RFID) tag is installed in a connector having an electrical contact member arranged therein. At the time of cleaning the endoscope, wireless communication is performed between an RFID communication device provided in a cleaning device and an RFID tag prior to the cleaning, and the RFID communication device receives information such as a model number and a serial number of the endoscope from the RFID tag.

SUMMARY

In some embodiments, an endoscope includes: a connector to which a waterproof cap ensuring watertightness is detachably attachable and in which an electrical contact member is arranged; an RFID tag that is arranged in the connector; an RFID tag storing member that has an opening in a part of the RFID tag storing member and is made of a conductive material, the RFID tag storing member being configured to store the RFID tag; an opening and closing member that is made of a conductive material shielding a radio wave, the opening and closing member being configured to open or close the opening; and a moving mechanism configured to move the opening and closing member to a position of releasing shielding of the radio wave in conjunction with attachment of the waterproof cap to the connector when the waterproof cap is mounted on the connector, and move the opening and closing member to a position of shielding the radio wave in conjunction with detachment of the waterproof cap from the connector when the waterproof cap is not mounted on the connector.

In some embodiments, provided is a waterproof cap of an endoscope detachably attached to a connector of the endoscope including an RFID tag storing member, an opening and closing member that is capable of opening and closing an opening of the RFID tag storing member, and a moving mechanism configured to move the opening and closing member. The waterproof cap includes an operating member configured to operate the moving mechanism with an operation of attaching or detaching the waterproof cap to and from the connector.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 5A is a view illustrating a first locked state of the waterproof cap attached to the first connector portion; FIG. 5B is a view illustrating transition from the first locked state to a second locked state of the waterproof cap attached to the first connector portion; FIG. 5C is a view illustrating the second locked state of the waterproof cap attached to the first connector portion;

FIG. 6 is a cross-sectional view illustrating a positional relationship between a first packing and a connecting portion in the first locked state;

DETAILED DESCRIPTION

Hereinafter, embodiments of an endoscope and a waterproof cap of an endoscope according to the disclosure will be described. Note that the disclosure is not limited to the present embodiments.

First Embodiment

Figure 1:
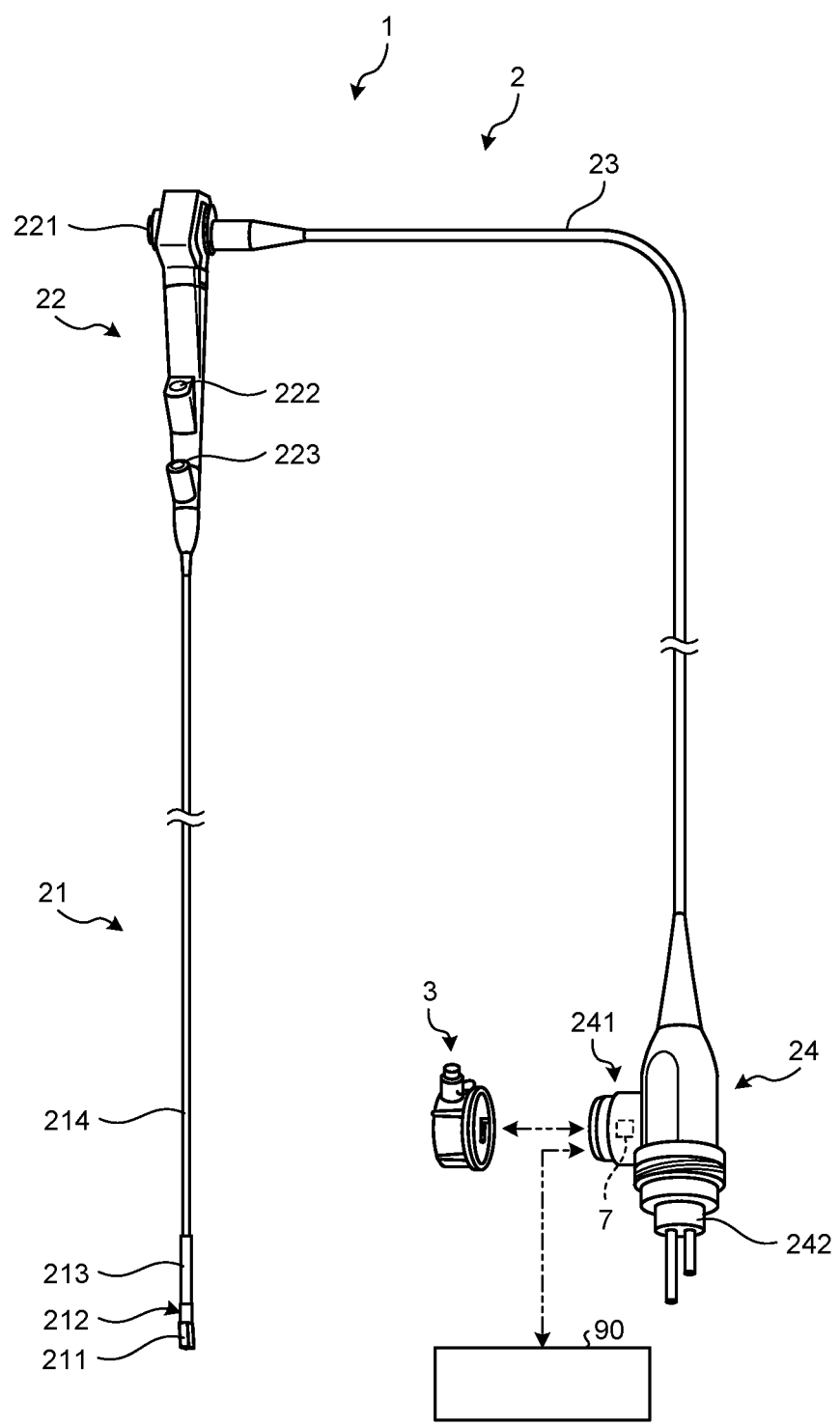
FIG. 1 is a view schematically illustrating an endoscope system according to a first embodiment.

FIG. 1 is a schematic view illustrating an endoscope system 1 according to a first embodiment. The endoscope system 1 is a system that uses properties of ultrasonic waves to apply the ultrasonic waves to a subject and visualize the reflection thereof. As illustrated in FIG. 1, the endoscope system 1 includes an endoscope 2 and a waterproof cap 3 attached to the endoscope 2. The endoscope 2 is an ultrasound endoscope which has a part that can be inserted into a subject and has a function of transmitting an ultrasound wave inside the subject and receiving reflection (echo) reflected by the subject to output an echo signal. The endoscope 2 is connectable to an image processing device 90, which receives the echo signal and generates an ultrasound image in response this echo signal, via a cable.

The endoscope 2 includes an ultrasound transducer 211, which converts an electrical pulse signal received from the processing device (not illustrated) into an ultrasound pulse and emits the converted signal to the subject, and converts the ultrasound echo reflected by the subject into an electrical echo signal expressed in a voltage change and outputs the converted signal, at a distal end portion thereof. The ultrasound transducer 211 may employ any one among a convex transducer, a linear transducer, and a radial transducer.

The endoscope 2 includes an imaging optical system and an imaging element, and can be inserted into a digestive tract (esophagus, stomach, duodenum, or large intestine) or a respiratory organ (trachea or bronchus) of the subject, and capture the digestive tract, the respiratory organ, and a surrounding organ thereof (pancreas, gallbladder, bile duct, biliary tract, lymph node, mediastinal organs, blood vessels, or the like).

As illustrated in FIG. 1, the endoscope 2 includes an insertion portion 21, an operating unit 22, a universal cord 23, and a connector 24. Note that a "distal end side" in the first embodiment means a side of a distal end of the insertion portion 21. In addition, a "proximal end side" in the first embodiment means a side separated from the distal end of the insertion portion 21.

The insertion portion 21 is a portion inserted inside the subject. As illustrated in FIG. 1, the insertion portion 21 includes a rigid member 212 that holds the ultrasound transducer 211 at the distal end, a bent portion 213 that is connected to a proximal end side of the rigid member 212 to be bendable, and a flexible tube portion 214 that is connected to the proximal end side of the bent portion 213 and has flexibility are provided.

Inside the insertion portion 21, a light guide to transmit the illumination light supplied from the light source device (not illustrated) and a plurality of signal cables to transmit various signals are wired, and a processing tool insertion passage, which causes a treatment tool to be inserted, is formed although not illustrated in detail.

The operating unit 22 is a portion that is connected to the proximal end side of the insertion portion 21 and receives various operations such as an angle operation, an air supply operation, a water supply operation, and a suction operation. As illustrated in FIG. 1, the operating unit 22 includes a bending knob 221 configured for a bending operation of the bent portion 213. In addition, in the operating unit 22, a treatment tool insertion port 222, configured to communicate with a treatment tool insertion passage formed in the insertion portion 21 and cause the treatment tool to be inserted into the treatment tool insertion passage, and an air and water supply port 223, configured to communicate with an air and water supply passage formed in the insertion portion 21 and cause a gas or liquid to flow through the air and water supply passage are formed. Note that, in another embodiment, an air and water supply port may be provided in a second connector portion 242 connected to a light source device (not illustrated) instead of the air and water supply port 223.

Inside the universal cord 23, cables that extend from the operating unit 22 and are formed by arranging a plurality of signal cables to transmit various signals and an optical fiber to transmit illumination light supplied from the light source device or the like are wired.

The connector 24 is provided at a distal end of the universal cord 23, and includes a first connector portion 241 and the second connector portion 242. The first connector portion 241 is connected with a connector portion of an ultrasound cable that holds the plurality of the signal cables and is connected to the image processing device 90. The second connector portion 242 is connected with the cable in which the optical fiber or the like is arranged and is connected to the light source device. In addition, an RFID tag 7 in which information such as a model name and a serial number of the endoscope 2 is stored is installed in the first connector portion 241 of the connector 24.

Figure 2:
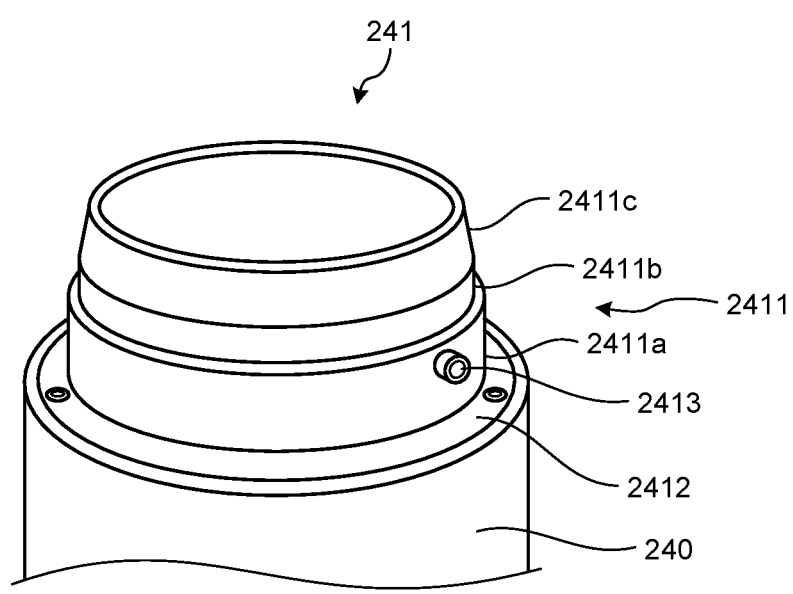
FIG. 2 is a perspective view schematically illustrating a first connector portion of the endoscope system according to the first embodiment.

Hereinafter, a structure of the first connector portion 241 will be described. FIG. 2 is a perspective view schematically illustrating the first connector portion 241 of the endoscope system 1 according to the first embodiment. The first connector portion 241 is an electrical connector configured for electrically connection with the plurality of the signal cables built in the universal cord 23. As illustrated in FIG. 2, the first connector portion 241 has a cylindrical shape that covers a terminal 70 (see FIG. 5A) which is an electrical contact member installed on a terminal installation wall portion 2414 and electrically connected to the plurality of the signal cable. Note that the terminal 70 is arranged in a state where the inside of the first connector portion 241 is airtightly closed with an O-ring or the like although a specific illustration is omitted.

The first connector portion 241 includes a connecting portion 2411 that is connected to the connector portion of the ultrasound cable connected to the image processing device 90, and an overhanging portion 2412 that overhangs from a proximal end of the connecting portion 2411 to the radially outer side. In the first connector portion 241, the overhanging portion 2412 fits into an opening that is formed in a connector case 240 constituting the connector (see FIG. 1), and the opening is airtightly closed by the O-ring or the like.

As illustrated in FIG. 2, the connecting portion 2411 includes a base 2411a, an airtight portion 2411b, a reduced diameter portion 2411c. The base 2411a has a cylindrical shape that extends from the overhanging portion 2412 in the axial direction. The airtight portion 2411b extends from the base 2411a in the axial direction to a side different from the overhanging portion 2412 side, forms a cylindrical shape having a smaller diameter than that of the base 2411a, and is airtightly connectable to the waterproof cap 3 to be described later. The reduced diameter portion 2411c is an end portion of the airtight portion 2411b, has a cylindrical shape extending from an end portion on a side different from the base 2411a side, and has a diameter of an outer peripheral surface decreasing toward the distal end. In the first embodiment, the airtight portion 2411b and the reduced diameter portion 2411c constitute a sleeve portion. In addition, two locking pins 2413 configured to lock the waterproof cap 3 (see FIG. 3) to the first connector portion 241 protrudes from an outer peripheral surface and is attached to the base 2411a.

Before and after ultrasound diagnosis in the subject, the ultrasound cable is removed from the first connector portion 241 in the endoscope 2, and cleaning and disinfection processing are performed. At this time, the waterproof cap 3 (see FIG. 3) is attached to the first connector portion 241 in order to exert two functions including a watertightness function of preventing a liquid such as water and a disinfectant from entering the inside of the first connector portion 241 and an airtightness function of preventing entry of a sterilized gas.

Figure 3:
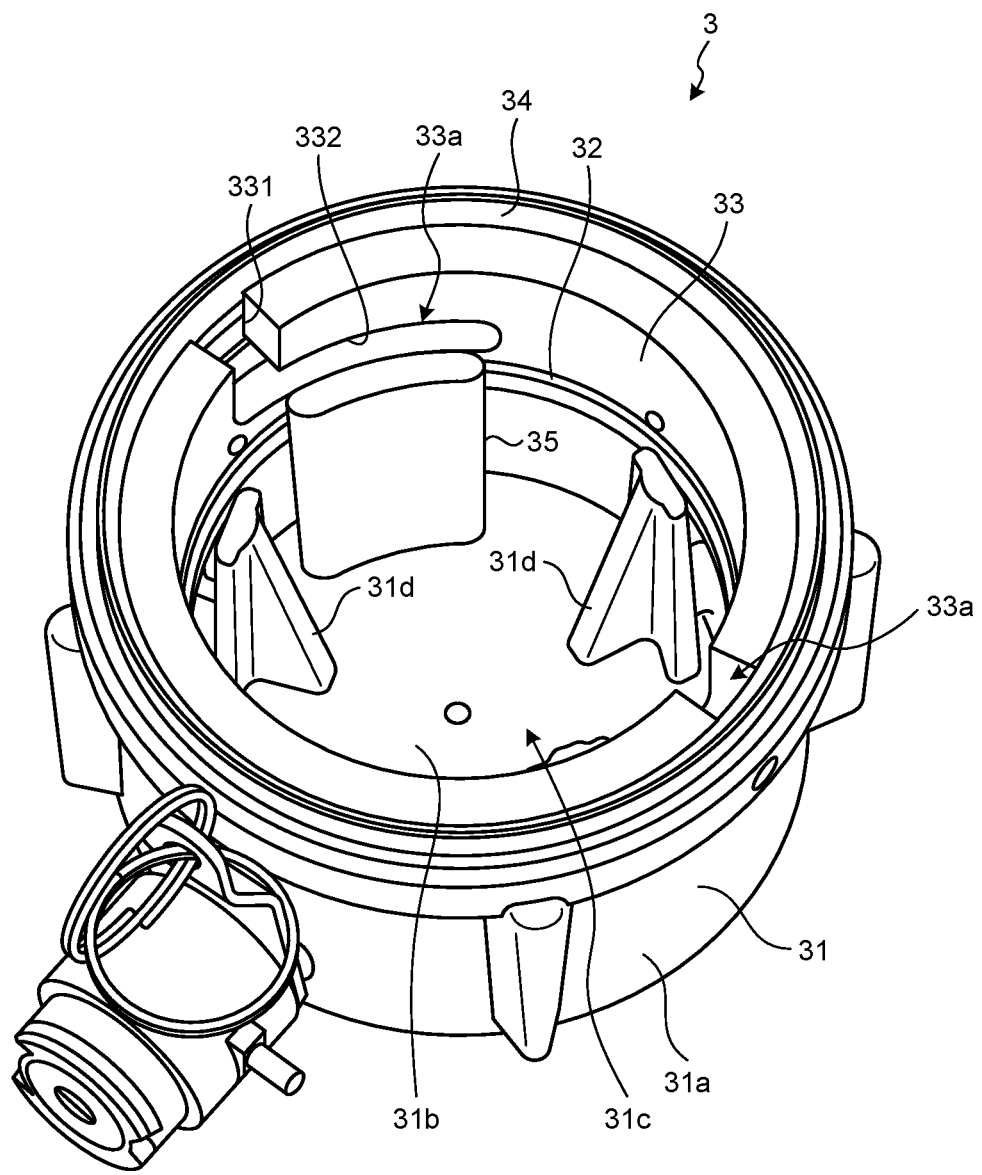
FIG. 3 is a perspective view illustrating an internal structure of a waterproof cap attached to the first connector portion.
Figure 4:
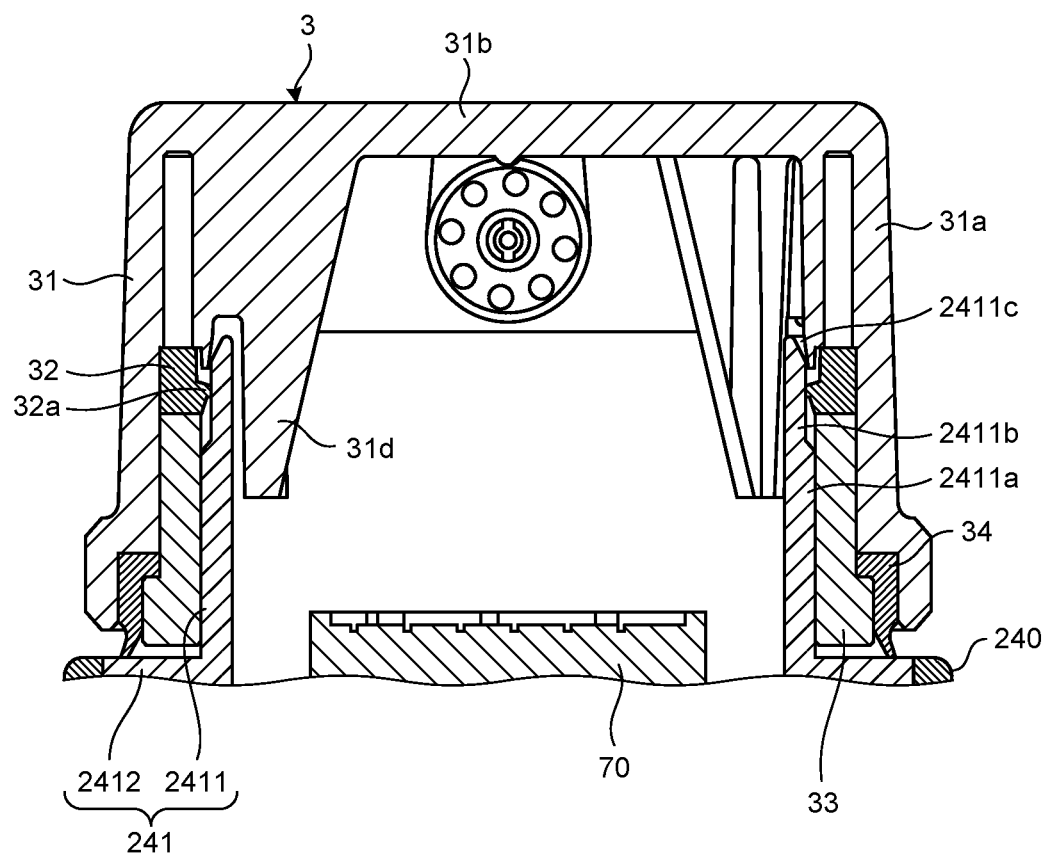
FIG. 4 is a cross-sectional view illustrating a state where the waterproof cap is attached to the first connector portion.

FIG. 3 is a perspective view illustrating an internal structure of the waterproof cap 3 attached to the first connector portion 241. FIG. 4 is a cross-sectional view illustrating a state where the waterproof cap 3 is attached to the first connector portion 241. As illustrated in FIGS. 3 and 4, the waterproof cap 3 includes a cap body 31, a first packing 32, a cam body 33 and a second packing 34.

The cap body 31 includes a cylindrical side wall portion 31a which enables insertion of the connecting portion 2411 and a bottom portion 31b that closes one end of the side wall portion 31a, and includes an opening portion 31c at the other end of the side wall portion 31a. A rib 31d is erected on the bottom portion 31b. Further, as illustrated in FIG. 4, when the waterproof cap 3 is attached to the first connector portion 241, the rib 31d accommodates a part of the connecting portion 2411 in a hollow space formed by the rib 31d and the side wall portion 31a. In addition, a cylindrical pin 35, which is an operating member that operates a moving mechanism to be described later in conjunction with an operation of attaching and detaching the waterproof cap 3 to and from the first connector portion 241, is erected on the bottom portion 31b.

The first packing 32 has a ring shape, and is attached to an inner surface of the side wall portion 31a. Further, the first packing 32 includes a convex portion 32a that abuts on an outer peripheral surface of the connecting portion 2411, specifically, an outer peripheral surface of the airtight portion 2411b and holds airtightness inside the first connector portion 241 when the waterproof cap 3 is attached to the first connector portion 241 as illustrated in FIG. 4.

The cam body 33 has a cylindrical shape that enables insertion of the connecting portion 2411, and is attached to the opening portion 31c side on the inner surface of the side wall portion 31a. As illustrated in FIG. 3, two locking grooves 33a into which two locking pins 2413 (see FIG. 2) are inserted, respectively, are formed in the cam body 33.

As illustrated in FIG. 3, each of the two locking grooves 33a forms a substantially L shape having a first locking groove 331 and a second locking groove 332. The first locking groove 331 extends from one end (end portion of the opening portion 31c side) toward the other end (end portion of the bottom portion 31b side). The second locking groove 332 extends from the first locking groove 331 in a rotational direction about a central axis of the cam body 33 to be inclined toward the bottom portion 31b side. In the first embodiment, a bayonet-type locking structure is adopted as a locking structure of the first connector portion 241 and the waterproof cap 3.

The second packing 34 has a ring shape, and a part thereof is inserted into a gap between the cam body 33 and the inner surface of the side wall portion 31a so that the second packing 34 is attached to the opening portion 31c. Further, the second packing 34 abuts on the overhanging portion 2412 and holds airtightness inside the first connector portion 241 when the waterproof cap 3 is attached to the first connector portion 241 as illustrated in FIG. 4.

Figure 5A:
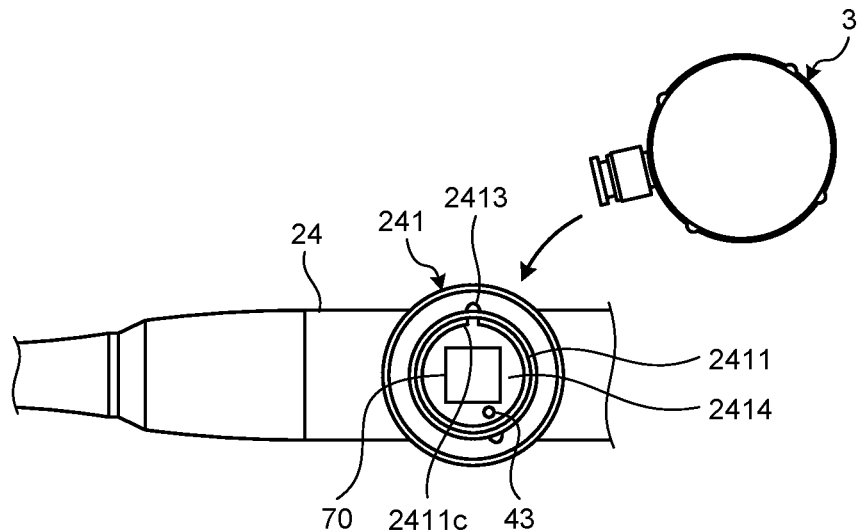
FIGS. 5A to 5C are views illustrating a locked state of the waterproof cap with respect to the first connector portion.
Figure 5B:
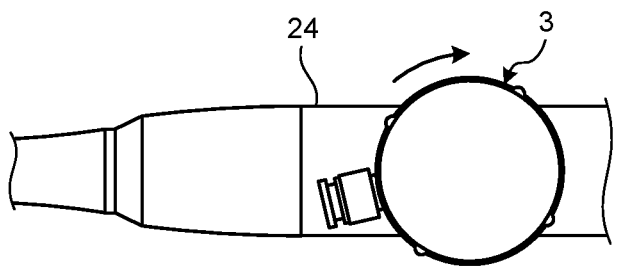
Figure 5C:
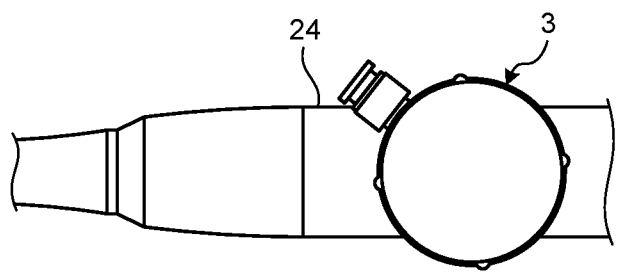

Subsequently, the attachment of the waterproof cap 3 with respect to the first connector portion 241 will be illustrated with reference to FIGS. 5A to 5C and 6. FIG. 5A is a view illustrating a first locked state of the waterproof cap 3 attached to the first connector portion 241. FIG. 5B is a view illustrating transition from the first locked state to a second locked state of the waterproof cap 3 attached to the first connector portion 241. FIG. 5C is a view illustrating the second locked state of the waterproof cap 3 attached to the first connector portion 241. FIG. 6 is a cross-sectional view illustrating a positional relationship between the first packing 32 and the connecting portion 2411 in the first locked state.

As illustrated in FIG. 5A, first, the waterproof cap 3 is fitted into the first connector portion 241 when the waterproof cap 3 is attached to the first connector portion 241. At this time, the locking pin 2413 is turned into the first locked state where the locking pin 2413 is accommodated in the first locking groove 331. In the first locked state, the convex portion 32a of the first packing 32 is arranged at a position of abutting on the reduced diameter portion 2411c or facing the reduced diameter portion 2411c as illustrated in FIG. 6. For this reason, the first connector portion 241 and the waterproof cap 3 are not set to the airtight state in the first locked state.

Further, the waterproof cap 3 is rotated with respect to the first connector portion 241 along a formation direction of the second locking groove 332 as illustrated in FIG. 5B. At this time, the locking pin 2413 moves along the second locking groove 332. As a result, the waterproof cap 3 is pushed into a direction of approaching the first connector portion 241. Hereinafter, a locked state when the locking pin 2413 is moved to an end portion of the second locking groove 332, the end portion on a side different from the first locking groove 331 side is referred to as the second locked state (see FIG. 5C). In the second locked state, a state where the convex portion 32a of the first packing 32 is arranged at a position of abutting on an outer peripheral surface of the airtight portion 2411b and the airtightness inside the first connector portion 241 is held is formed as illustrated in FIG. 4. In this second locked state, cleaning and disinfection of the endoscope 2 are implemented using a cleaning and disinfecting device 101 to be described later (see FIG. 7).

Figure 7:
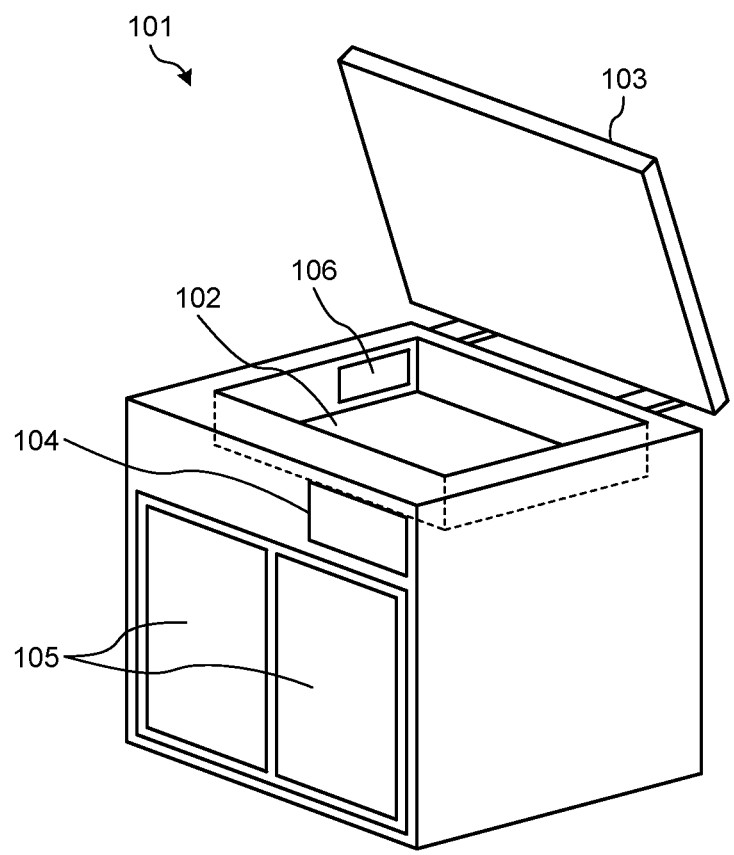
FIG. 7 is a perspective view illustrating a schematic configuration of a cleaning and disinfecting device according to the first embodiment.

FIG. 7 is a perspective view illustrating a schematic configuration of the cleaning and disinfecting device 101 according to the first embodiment. The cleaning and disinfecting device 101 is provided with: a cleaning tank 102 configured to clean and disinfect the endoscope 2; an opening and closing cover 103 configured to cover the cleaning tank 102 and prevent scattering of a liquid agent such as a cleaning solution and a disinfectant; a controller panel 104 configured to set a cleaning and disinfecting program or the like; and a liquid agent tank 105 configured to store the cleaning solution and the disinfectant. In addition, an inner wall of the cleaning tank 102 in the cleaning and disinfecting device 101 is provided with an RFID communication device 106 configured to perform wirelessly communication with the RFID tag 7 installed in the first connector portion 241 of the endoscope 2 to read information such as a model name and a serial number of the endoscope 2.

Next, an operation of the cleaning and disinfecting device 101 will be described. First, the waterproof cap 3 is connected to the first connector portion 241 of the endoscope 2. Further, the endoscope 2 on which the waterproof cap 3 is mounted is installed in the cleaning tank 102 by opening the opening and closing cover 103 of the cleaning and disinfecting device 101. Thereafter, when the opening and closing cover 103 is closed and a power supply of the cleaning and disinfecting device 101 is turned on, the cleaning and disinfecting device 101 automatically activates an RFID system, performs wireless communication between the RFID communication device 106 and the RFID tag 7 of the endoscope 2, and reads information such as the model name and the serial number of the endoscope 2 from the RFID tag 7 to the RFID communication device 106. The cleaning and disinfecting device 101 executes the cleaning and disinfecting program, which is set in advance, in response to the information read by the RFID communication device 106, and feeds the cleaning solution and the disinfectant from the liquid agent tank 105 to the cleaning tank 102 according to the cleaning and disinfecting program to implement cleaning and disinfection of the endoscope 2. Since the wireless communication is performed between the RFID tag 7 of the endoscope 2 installed in the cleaning tank 102 and the RFID communication device 106 in this manner, the cleaning and disinfecting device 101 according to the first embodiment can start the cleaning and disinfection of the endoscope 2.

Note that, in another embodiment, communication between an RFID communication device outside the cleaning tank 102, instead of the RFID communication device 106, and the RFID tag 7 of the endoscope 2 on which the waterproof cap 3 is mounted may be performed to read information from the RFID tag 7 to the outside of the cleaning tank 102. Further, the endoscope 2 on which the waterproof cap 3 is mounted is installed inside the cleaning tank 102 after the end of the communication, and then, the cleaning and disinfection of the endoscope 2 is performed by the cleaning and disinfecting device 101.

Figure 8:
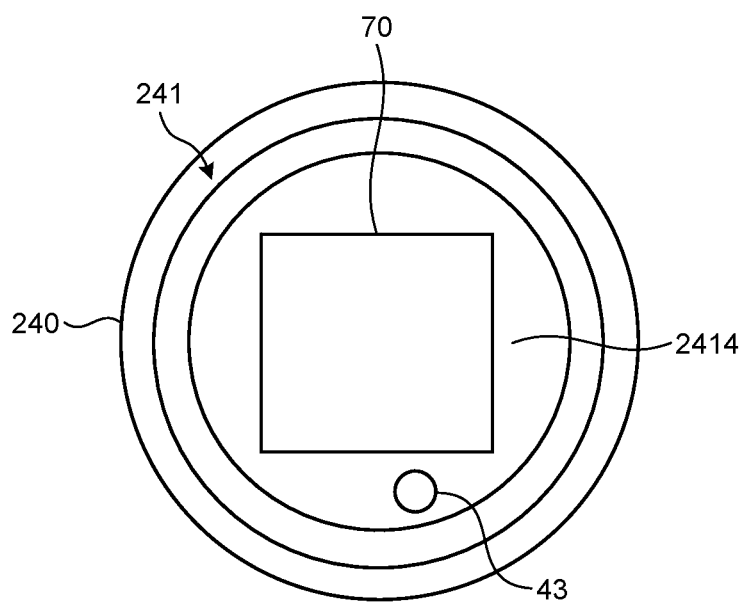
FIG. 8 is a schematic view of the first connector portion as viewed from the top.
Figure 9:
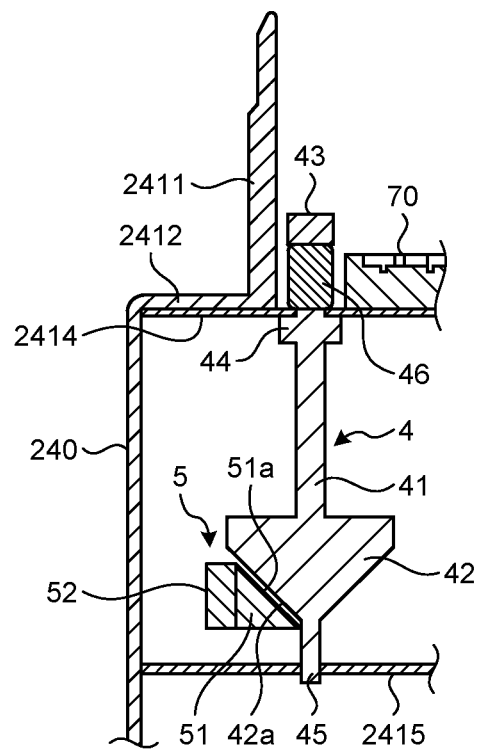
FIG. 9 is a cross-sectional view of the first connector portion when the waterproof cap is not mounted on the first connector portion.
Figure 10:
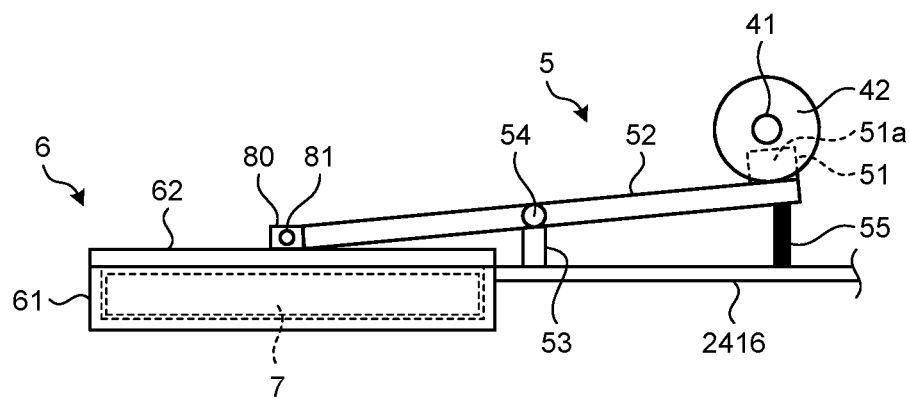
FIG. 10 is a side view of an RFID tag storing member and the vicinity thereof when the waterproof cap is not mounted on the first connector portion.
Figure 11:
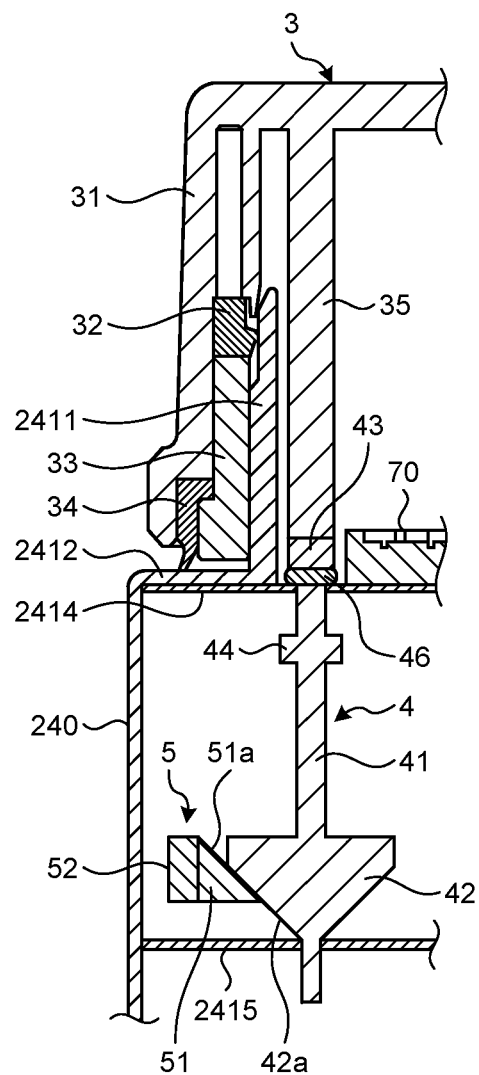
FIG. 11 is a cross-sectional view of the first connector portion when the waterproof cap is mounted on the first connector portion.
Figure 12:
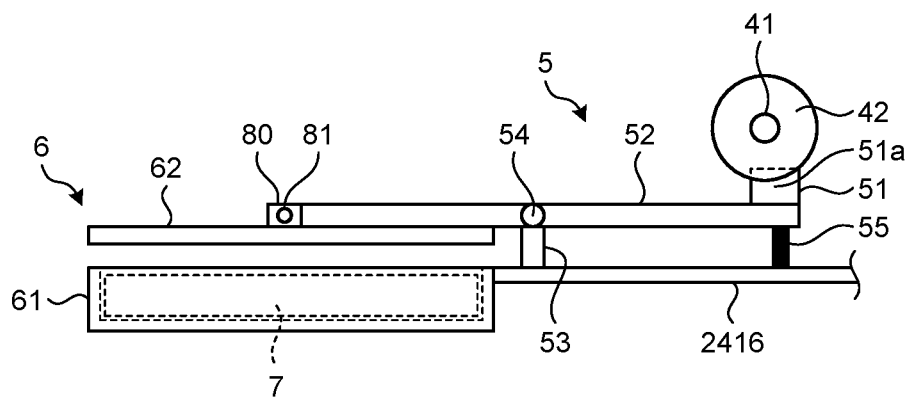
FIG. 12 is a side view of the RFID tag storing member and the vicinity thereof when the waterproof cap is mounted on the first connector portion.

FIG. 8 is a schematic view of the first connector portion 241 as viewed from the top. FIG. 9 is a cross-sectional view of the first connector portion 241 when the waterproof cap 3 is not mounted on the first connector portion 241. FIG. 10 is a side view of an RFID tag storing member 6 and the vicinity thereof when the waterproof cap 3 is not mounted on the first connector portion 241. FIG. 11 is a cross-sectional view of the first connector portion 241 when the waterproof cap 3 is mounted on the first connector portion 241. FIG. 12 is a side view of the RFID tag storing member 6 and the vicinity thereof when the waterproof cap 3 is mounted on the first connector portion 241.

In the first embodiment, the RFID tag 7 which can communicate with the RFID communication device 106 is arranged more inside than the terminal installation wall portion 2414 of the first connector portion 241 as illustrated in the FIG. 8. As illustrated in FIG. 10, the RFID tag 7 is stored in the RFID tag storing member 6 provided to a wall portion 2416 of the first connector portion 241. The RFID tag storing member 6 includes: a metallic storage body case 61 inside which the RFID tag 7 is mounted and an opening and closing lid 62 which is a metallic sealing member capable of opening and closing the storage body case 61. Note that the storage body case 61 and the opening and closing lid 62 are not limited to be made of metal, but only have to be produced using conductive materials. The storage body case 61 has a box shape of which a surface facing the opening and closing lid 62 is open, and is fixed to the wall portion 2416 of the first connector portion 241 existing in a direction orthogonal to the axial direction of the waterproof cap 3. The opening and closing lid 62 has a plate shape, and completely closes the opening at the time of closing the storage body case 61.

The opening and closing lid 62 is movable between a position of sealing the RFID tag storing member 6 and a position of releasing the sealing of the RFID tag storing member 6 by a moving mechanism constituted by a slider 4 illustrated in FIG. 9 and a link mechanism 5 illustrated in FIG. 10.

As illustrated in FIG. 9, the slider 4 includes a shaft 41, a first cam portion 42, a shaft rear end portion 43, a regulating portion 44, a shaft distal end portion 45 and the like. As illustrated in FIG. 8 and FIG. 9, the shaft 41 of the slider 4 penetrates through a hole formed in the terminal installation wall portion 2414 with the shaft rear end portion 43 positioned closer to the terminal 70 than the terminal installation wall portion 2414. In the axial direction of the slider 4, a spring member 46 is arranged between the shaft rear end portion 43 and the terminal installation wall portion 2414. In addition, the shaft 41 of the slider 4 is provided with the regulating portion 44 that regulates movement of the slider 4 in the axial direction by coming into contact with a side of the terminal installation wall portion 2414 opposite to the terminal 70 side. A wall portion 2415 having a hole through which the shaft distal end portion 45 of the slider 4 penetrates is provided inside the first connector portion 241 with respect of the terminal installation wall portion 2414. The first cam portion 42 of the slider 4 is provided slightly closer to the shaft rear end portion 43 side rather than the shaft distal end portion 45. The first cam portion 42 has a conical shape having a first cam surface 42a which is inclined such that a diameter of the conical shape increases from the shaft distal end portion 45 side toward the shaft rear end portion 43 side in the axial direction.

As illustrated in FIG. 10, the link mechanism 5 is provided with a second cam portion 51, a rotating rod 52, a supporting portion 53, a rotating shaft 54, and the like. The rotating rod 52 has a long rod shape, and is supported to be rotatable about the rotating shaft 54 by the supporting portion 53 provided on the wall portion 2416 of the first connector portion 241 at a substantially center in a longitudinal direction of the rotating rod 52. One end portion of the rotating rod 52 is provided with the second cam portion 51 having a second cam surface 51a which can come into contact with the first cam surface 42a of the first cam portion 42. The second cam surface 51a of the second cam portion 51 extends in a direction orthogonal to the longitudinal direction of the rotating rod 52. In addition, a spring member 55 that biases the rotating rod 52 to the first cam portion 42 side is provided between the one end portion of the rotating rod 52 and the wall portion 2416. Another end portion of the rotating rod 52 on a side opposite to the second cam portion 51 side is connected to a hinge portion 80 to be rotatable about a rotating shaft 81. The hinge portion 80 is provided on a surface of the opening and closing lid 62 on a side opposite to a side of the storage body case 61.

Next, the sealing of the RFID tag storing member 6 and the releasing of the sealing in conjunction with the attachment and detachment of the waterproof cap 3 to and from the first connector portion 241 will be described. Note that, as illustrated in FIG. 10, the opening and closing lid 62 closes the storage body case 61, and the RFID tag storing member 6 is sealed in the state where the waterproof cap 3 is not mounted on the first connector portion 241. If the RFID tag storing member 6 is sealed, a radio wave is shielded by the storage body case 61 and the opening and closing lid 62. Therefore, it is difficult for the RFID tag 7 to perform wireless communication with the RFID communication device 106.

First, an operation at the time of releasing the sealing of the RFID tag storing member 6 will be described. Before the endoscope 2 is installed in the cleaning tank 102 of the cleaning and disinfecting device 101, the waterproof cap 3 is mounted on the first connector portion 241, and the waterproof cap 3 is rotated to close the first connector portion 241 for the purpose of transition from the first locked state to the second locked state. Then, the shaft rear end portion 43 of the slider 4 is pushed against an elastic force of the spring member 46 by the pin 35 provided on the bottom portion 31b of the waterproof cap 3 as illustrated in FIG. 11. As a result, the slider 4 moves to the wall portion 2415 side, and the second cam surface 51a of the second cam portion 51 is pushed in the direction orthogonal to the axial direction of the slider by the first cam surface 42a of the first cam portion 42. Further, the rotating rod 52 rotates about the rotating shaft 54 in the clockwise direction in FIG. 12, and as illustrated in FIG. 12, the opening and closing lid 62 connected to the rotating rod 52 by the hinge portion 80 is separated from the storage body case 61 to open the storage body case 61. As a result, the sealing of the RFID tag storing member 6 is released, the RFID tag 7 is exposed from the opening of the storage body case 61, the radio wave is not shielded by the storage body case 61 and the opening and closing lid 62, and the RFID tag 7 can wirelessly communicate with the RFID communication device 106.

Next, an operation at the time of sealing the RFID tag storing member 6 will be described. After the cleaning and disinfection of the cleaning and disinfecting device 101 are implemented, the waterproof cap 3 is rotated with respect to the endoscope 2 taken out from the cleaning tank 102 to cause transition from the second locked state to the first locked state, and the waterproof cap 3 is removed from the first connector portion 241. At this time, if the waterproof cap 3 is rotated for the transition from the second locked state to the first locked state, the shaft rear end portion 43 of the slider 4 pushed by the pin 35 of the waterproof cap 3 is pushed up by the elastic force of the spring member 46. As a result, the slider 4 moves toward the terminal installation wall portion 2414, and accordingly, the second cam surface 51a of the second cam portion 51 is not pushed by the first cam surface 42a of the first cam portion 42. Further, the rotating rod 52 rotates about the rotating shaft 54 in the counter-clockwise direction in FIG. 10 by an elastic force of the spring member 55, and the opening and closing lid 62 connected to the rotating rod 52 by the hinge portion 80 closes the storage body case 61. As a result, the opening of the storage body case 61 is closed by the opening and closing lid 62, and the RFID tag storing member 6 is sealed. Thus, the radio wave is shielded by the storage body case 61 and the opening and closing lid 62, and it is difficult for the RFID tag 7 to perform the wireless communication with the RFID communication device 106.

It is desirable to provide the pin 35 of the waterproof cap 3 in the vicinity of the locking groove 33a (second locking groove 332). With such an arrangement, it is possible to prevent the waterproof cap 3 from being inclined and attached since the locking pin 2413 is inserted into the locking groove 33a (second locking groove 332) even if the pin 35 of the waterproof cap 3 receives the elastic force of the spring member 46.

In the endoscope 2 according to the first embodiment, it is difficult to perform the wireless communication between the RFID tag 7 and the RFID communication device 106 if the attachment of the waterproof cap 3 to the first connector portion 241 is missed when the cleaning and disinfection of the endoscope 2 is performed by the cleaning and disinfecting device 101. Therefore, it is difficult for the cleaning and disinfecting device 101 to clean and disinfect the endoscope 2 by executing the cleaning and disinfecting program. Thus, the endoscope 2 according to the first embodiment can prevent the cleaning and disinfecting device 101 from performing cleaning and disinfection in the state where the attachment of the waterproof cap 3 is missed.

Second Embodiment

Next, the endoscope 2 according to a second embodiment will be described with reference to FIGS. 13 to 16. Note that parts of the endoscope 2 according to the second embodiment common to those of the endoscope 2 according to the first embodiment will not be described as appropriate.

Figure 13:
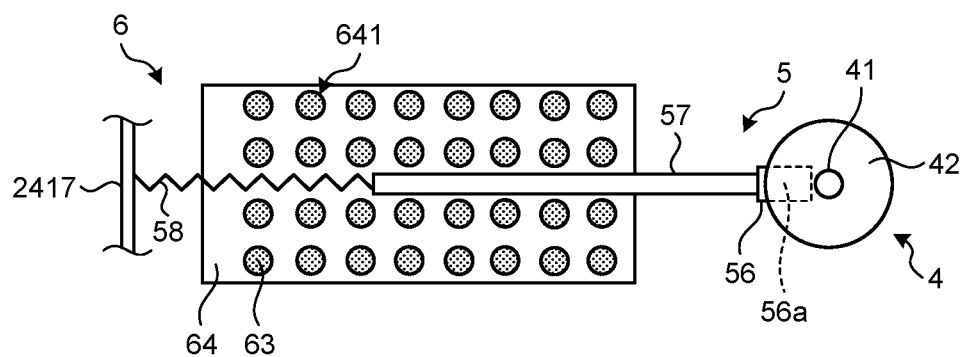
FIG. 13 is a top view of an RFID tag storing member and the vicinity thereof when a waterproof cap is not mounted on a first connector portion.
Figure 14:
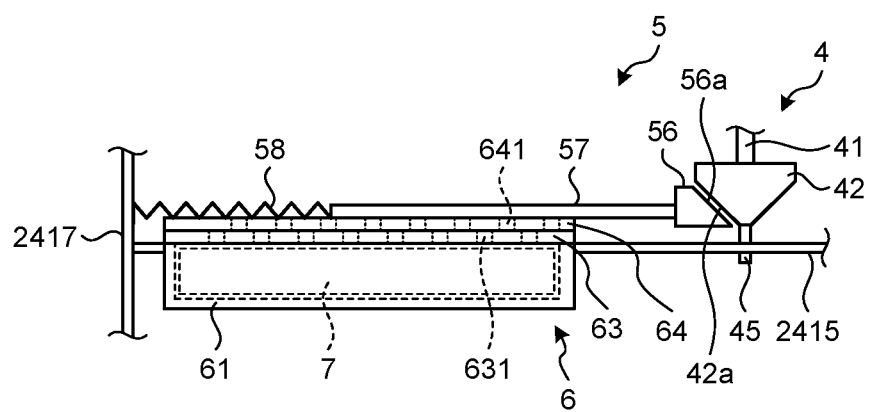
FIG. 14 is a side view of the RFID tag storing member and the vicinity thereof when the waterproof cap is not mounted on the first connector portion.
Figure 15:
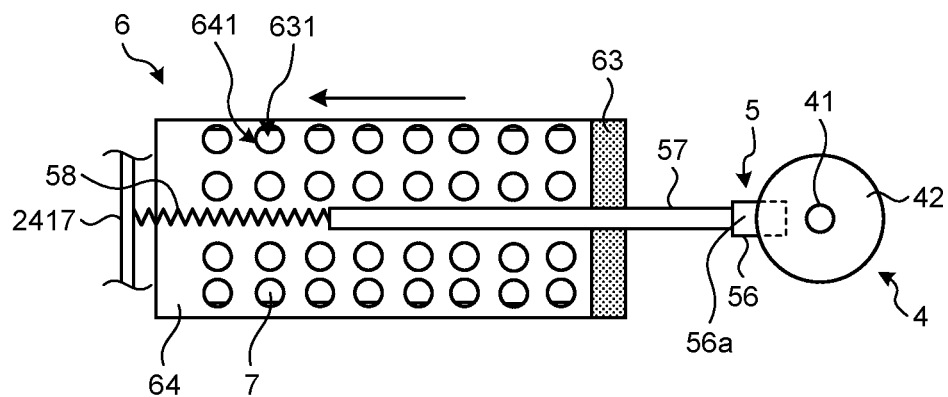
FIG. 15 is a top view of the RFID tag storing member and the vicinity thereof when the waterproof cap is mounted on the first connector portion.
Figure 16:
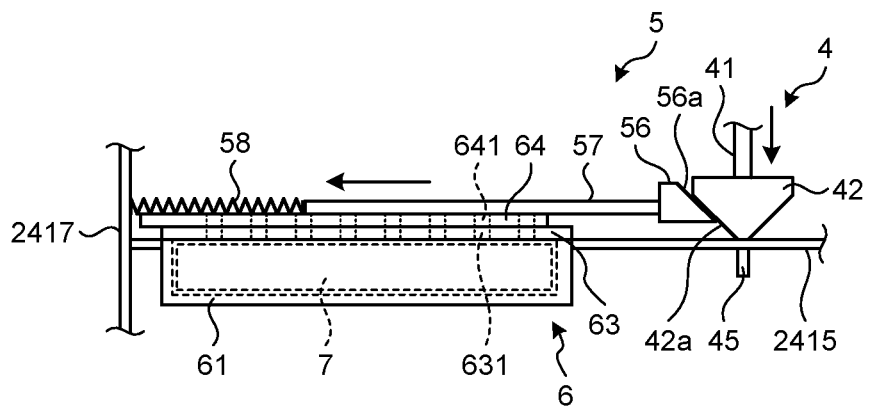
FIG. 16 is a side view of the RFID tag storing member and the vicinity thereof when the waterproof cap is mounted on the first connector portion.

FIG. 13 is a top view of the RFID tag storing member 6 and the vicinity thereof when the waterproof cap 3 is not mounted on the first connector portion 241. FIG. 14 is a side view of the RFID tag storing member 6 and the vicinity thereof when the waterproof cap 3 is not mounted on the first connector portion 241. FIG. 15 is a top view of the RFID tag storing member 6 and the vicinity thereof when the waterproof cap 3 is attached to the first connector portion 241. FIG. 16 is a side view of the RFID tag storing member 6 and the vicinity thereof when the waterproof cap 3 is mounted on the first connector portion 241.

In the endoscope 2 according to the second embodiment, the link mechanism 5 includes a third cam portion 56, a slide rod 57, and a spring member 58 as illustrated in FIGS. 13 and 14. The slide rod 57 has a long rod shape and is provided with the third cam portion 56 having a third cam surface 56a, which can come into contact with the first cam surface 42a of the first cam portion 42, at an end surface on one end portion side in the longitudinal direction. The third cam surface 56a of the third cam portion 56 extends in the longitudinal direction of the slide rod 57. In addition, the spring member 58 biasing the slide rod 57 toward the first cam portion 42 side is provided between an end surface on the other end portion side of the slide rod 57 and a wall portion 2417 in the first connector portion 241.

In addition, the RFID tag storing member 6 includes the metallic storage body case 61, a metallic fixed lid 63, and a metallic movable lid 64 in the endoscope 2 according to second embodiment as illustrated in FIGS. 13 and 14. Note that the storage body case 61, the fixed lid 63, and the movable lid 64 are not limited to be made of metal, but only have to be produced using conductive materials. The storage body case 61 is fixed to the wall portion 2415 existing in the axial direction of the waterproof cap 3 in the first connector portion 241. The fixed lid 63 is fixed to the storage body case 61 to cover the opening of the storage body case 61. The fixed lid 63 is formed with a plurality of through-holes 631 that enables communication between the inside and the outside of the storage body case 61.

The movable lid 64 is superimposed on a surface on a side opposite to the storage body case 61 side of the fixed lid 63 in a close-contact manner. The slide rod 57 of the link mechanism 5 is connected to a surface on a side opposite to the fixed lid 63 side of the movable lid 64 Further, the movable lid 64 is movable to slide on the fixed lid 63 in conjunction with displacement of the slide rod 57. The movable lid 64 is formed with a plurality of through-holes 641 that enables communication between the inside and outside of storage body case 61.

When the waterproof cap 3 is not mounted on the first connector portion 241 as illustrated in FIGS. 13 and 14, the plurality of the through-holes 631 opened in the fixed lid 63 and the plurality of the through-holes 641 opened in the movable lid 64 are misaligned and do not communicate with each other. As a result, the opening of the storage body case 61 is closed by the fixed lid 63 and the movable lid 64 so that the RFID tag storing member 6 is sealed. Therefore, a radio wave is shielded by the storage body case 61, the fixed lid 63, and the movable lid 64, and it is difficult for the RFID tag 7 to wirelessly communicate with the RFID communication device 106.

If the waterproof cap 3 is mounted on the first connector portion 241 and the waterproof cap 3 is rotated to close the first connector portion 241, the shaft rear end portion 43 of the slider 4 is pushed by the pin 35 of the waterproof cap 3, and the slider 4 is pushed against the elastic force of the spring member 46, which is similar to the first embodiment. As a result, the third cam surface 56a of the third cam portion 56 is pushed in the longitudinal direction of the slide rod 57 by the first cam surface 42a of the first cam portion 42. Further, the slide rod 57 is pushed against the elastic force of the spring member 58, and the movable lid 64 connected to the slide rod 57 slides on the fixed lid 63 as illustrated in FIGS. 15 and 16. As a result, the plurality of the through-holes 631 opened in the fixed lid 63 and the plurality of the through-holes 641 opened in the movable lid 64 are aligned in position and communicate with each other. Therefore, the inside and the outside of the storage body case 61 communicate with each other by the plurality of the through-holes 631 and the plurality of the through-holes 641, the RFID tag 7 is exposed, a radio wave is not shielded, and the RFID tag 7 can wirelessly communicate with the RFID communication device 106.

As described above, in the endoscope 2 according to the second embodiment, the plurality of the through-holes 641 and the plurality of the through-holes 631 do not communicate with each other, and the RFID tag storing member 6 is in the sealed state in the state where the attachment of the waterproof cap 3 is missed. Thus, it is difficult to perform the wireless communication between the RFID tag 7 and the RFID communication device 106 so that it is possible to prevent the cleaning and disinfecting device 101 from performing the cleaning and disinfection.

Note that the fixed lid 63 and the movable lid 64 are formed with the plurality of the through-holes 631 and the plurality of the through-hole 641, respectively, in the second embodiment, but the disclosure is not limited thereto. For example, one or more through-holes 631 and one or more through-holes 641 may be opened in the fixed lid 63 and the movable lid 64, respectively. In addition, the plurality of through-holes 631 and the plurality of the through-holes 641 are arranged side by side to be aligned vertically and horizontally with respect to the fixed lid 63 and the movable lid 64 in the second embodiment, but the disclosure is not limited thereto. For example, the through-holes 631 and the through-holes 641 may be arranged with respect to the fixed lid 63 and the movable lid 64 in a staggered manner (zigzag shape). Further, each of the through-hole 631 and the through-hole 641 has a circular shape in the second embodiment, but the disclosure is not limited thereto. For example, each of the through-hole 631 and the through-hole 641 may have a slit shape.

Third Embodiment

Next, the endoscope 2 according to a third embodiment will be described with reference to FIGS. 17 to 20. Note that parts of the endoscope 2 according to the third embodiment common to those of the endoscope 2 according to the first embodiment will not be described as appropriate.

Figure 17:
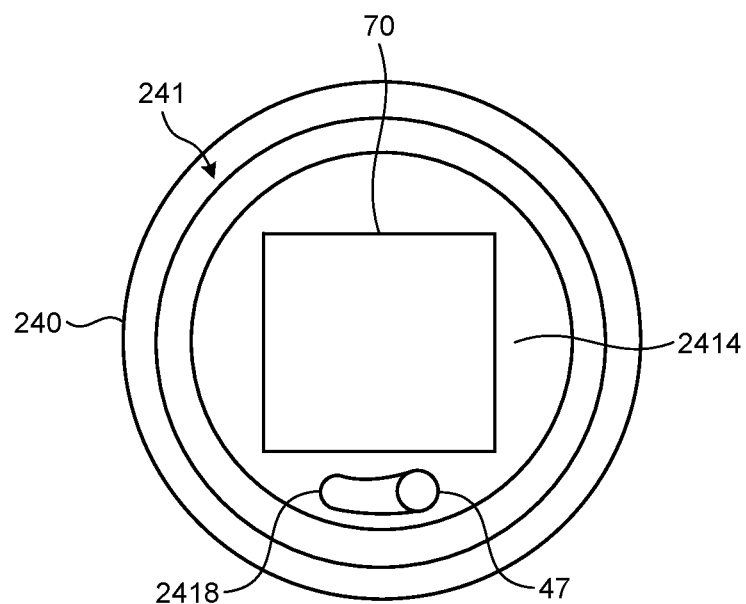
FIG. 17 is a schematic view of a first connector portion as viewed from the top when a waterproof cap is not mounted on the first connector portion.
Figure 18:
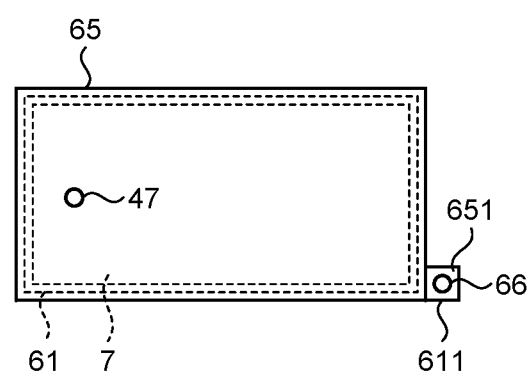
FIG. 18 is a top view of an RFID tag storing member when the waterproof cap is not mounted on the first connector portion.
Figure 19:
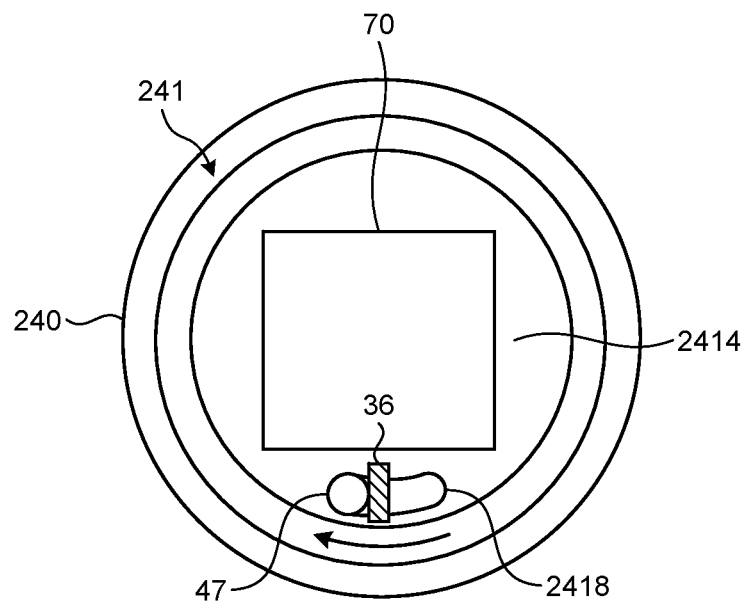
FIG. 19 is a schematic view of the first connector portion as viewed from the top when the waterproof cap is mounted on the first connector portion.
Figure 20:
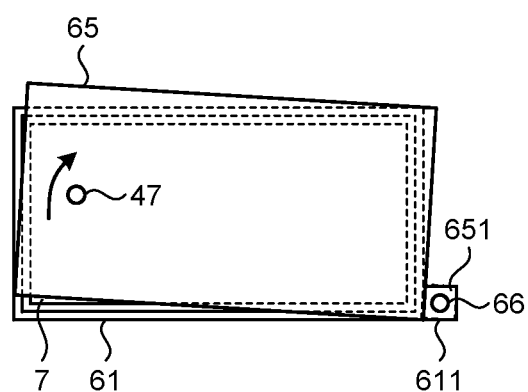
FIG. 20 is a top view of the RFID tag storing member when the waterproof cap is mounted on the first connector portion.

FIG. 17 is a schematic view of the first connector portion 241 as viewed from the top when the waterproof cap 3 is not mounted on the first connector portion 241. FIG. 18 is a top view of the RFID tag storing member 6 when the waterproof cap 3 is not mounted on the first connector portion 241. FIG. 19 is a schematic view of the first connector portion 241 as viewed from the top when the waterproof cap 3 is mounted on the first connector portion 241. Note that parts of the waterproof cap 3 other than a pin 36 to be described later are not illustrated in FIG. 19. FIG. 20 is a top view of the RFID tag storing member 6 when the waterproof cap 3 is mounted on the first connector portion 241.

As illustrated in FIG. 17, an arc-shaped elongated hole 2418 is opened in the terminal installation wall portion 2414 of the first connector portion 241 in the endoscope 2 according to the third embodiment. A pin 47 penetrates through the elongated hole 2418, and one end portion of the pin 47 extends to a side closer to the terminal 70 than the terminal installation wall portion 2414.

In addition, the RFID tag storing member 6 is provided with the metallic storage body case 61 and a metallic rotating lid 65 in the endoscope 2 according to the third embodiment as illustrated in FIG. 18. Note that the storage body case 61 and the rotating lid 65 are not limited to be made of metal, but only have to be produced using conductive materials. The storage body case 61 is fixed to a wall portion (not illustrated) existing in the axial direction of the waterproof cap 3 in the first connector portion 241. The storage body case 61 and the rotating lid 65 are respectively provided with a case-side supporting portion 611 and a rod-side supporting portion 651 connected by a rotating shaft 66. As a result, the rotating lid 65 is rotatable about the rotating shaft 66 with respect to the storage body case 61. The other end portion of the cylindrical pin 47 is connected to a surface of the rotating lid 65 on a side opposite to the storage body case 61 side.

In the endoscope 2 according to the third embodiment, a moving mechanism that moves the rotating lid 65 is constituted by the pin 47, the elongated hole 2418, the case-side supporting portion 611, the rod-side supporting portion 651, the rotating shaft 66, and the like. Further, the moving mechanism allows the rotating lid 65 to move between a position of closing the storage body case 61 to seal the RFID tag storing member 6 and a position of opening the storage body case 61 to release the sealing of the RFID tag storing member 6.

As illustrated in FIG. 18, the rotating lid 65 closes the storage body case 61, the opening of the storage body case 61 is closed by the rotating lid 65, and the RFID tag storing member 6 is sealed when the waterproof cap 3 is not mounted on the first connector portion 241. Therefore, a radio wave is shielded by the storage body case 61 and the rotating lid 65, and it is difficult for the RFID tag 7 to wirelessly communicate with the RFID communication device 106.

Note that, as illustrated in FIG. 19, the flat-plated pin 36, which is an operating member that operates the moving mechanism in conjunction with the attaching and detaching operation with respect to the first connector portion 241, is erected on the bottom portion 31*b* in the waterproof cap 3 according to the third embodiment (see FIG. 3). The pin 36 of the waterproof cap 3 pushes one end portion of the pin 47 exposed from the elongated hole 2418 from the lateral side to move the pin 47 along the elongated hole 2418 in the rotating direction of the waterproof cap 3 when the waterproof cap 3 is mounted on the first connector portion 241 and the waterproof cap 3 is rotated for the purpose of transition from the first locked state to the second locked state as described above. As a result, the rotating lid 65 connected to the other end portion of the pin 47 rotates about the rotating shaft 66 in the arrow direction in FIG. 20 with respect to the storage body case 61, and the storage body case 61 is open so that the sealing of the RFID tag storing member 6 is released. As a result, the RFID tag 7 is exposed from the opening of the storage body case 61, a radio wave is not shielded, and the RFID tag 7 can wirelessly communicate with the RFID communication device 106.

As described above, in the endoscope 2 according to the third embodiment, the rotating lid 65 closes the storage body case 61, and the RFID tag storing member 6 is in the sealed state in the state where the attachment of the waterproof cap 3 is missed. Thus, it is difficult to perform the wireless communication between the RFID tag 7 and the RFID communication device 106 so that it is possible to prevent the cleaning and disinfecting device 101 from performing the cleaning and disinfection.

Note that, in the endoscope 2 according to each of the above-described embodiments, it is desirable that the sealing state of the RFID tag storing member 6 be released when the waterproof cap 3 completely closes the first connector portion 241, in other words, when the waterproof cap 3 is in the second locked state with respect to the first connector portion 241.

An endoscope and a waterproof cap of an endoscope according to the disclosure achieve an effect that can prevent cleaning from being performed in a state where attachment of the waterproof cap is missed.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
a connector to which a waterproof cap ensuring watertightness is detachably attachable and in which an electrical contact member is arranged;
an RFID tag that is arranged in the connector;
an RFID tag storing member that has an opening in a part of the RFID tag storing member and is made of a conductive material, the RFID tag storing member being configured to store the RFID tag;
an opening and closing member that is made of a conductive material shielding a radio wave, the opening and closing member being configured to open or close the opening; and
a moving mechanism configured to
move the opening and closing member to a position of releasing shielding of the radio wave in conjunction with attachment of the waterproof cap to the connector when the waterproof cap is mounted on the connector, and
move the opening and closing member to a position of shielding the radio wave in conjunction with detachment of the waterproof cap from the connector when the waterproof cap is not mounted on the connector.

2. The endoscope according to claim 1, wherein
the opening and closing member is a sealing member configured to close the opening to seal the RFID tag storing member, and
sealing of the RFID tag storing member by the sealing member causes the shielding of the radio wave, and releasing of the sealing causes the releasing of the shielding of the radio wave.

3. The endoscope according to claim 2, wherein
the sealing member is capable of opening and closing the RFID tag storing member,
the sealing member is configured to close the RFID tag storing member to seal the RFID tag storing member when the waterproof cap is not mounted on the connector, and
the sealing member is configured to open the RFID tag storing member to release the sealing of the RFID tag storing member when the waterproof cap is mounted on the connector.

4. The endoscope according to claim 2, wherein
the sealing member includes:
a first plate-shaped member that is superimposed on the RFID tag storing member in a close-contact manner to cover the opening; and
a second plate-shaped member that is slidable with respect to the first plate-shaped member by the moving mechanism and is superimposed on the first plate-shaped member in a close-contact manner,
the first plate-shaped member has one or more first holes penetrating in a thickness direction of the first plate-shaped member,
the second plate-shaped member has one or more second holes penetrating in a thickness direction of the second plate-shaped member,
the first hole and the second hole do not communicate with each other and the RFID tag storing member is sealed when the waterproof cap is not mounted on the connector, and
the first hole and the second hole communicate with each other and the sealing of the RFID tag storing member is released when the waterproof cap is mounted on the connector.

5. The endoscope according to claim 3, wherein
the moving mechanism includes:
a first moving member that is connectable to the waterproof cap and has a first cam portion; and
a second moving member that has a second cam portion capable of coming into contact with the first cam portion, and
when the waterproof cap is mounted on the connector, the first moving member is pushed by the waterproof cap in a direction of mounting the waterproof cap to the connector to cause the first cam portion to push the second cam portion and thereby displace the second moving member to move the sealing member.

6. The endoscope according to claim 3, wherein
the waterproof cap is detachably attachable by rotation with respect to the connector, and the moving mechanism includes a displacing member configured to displace in conjunction with the rotation of the waterproof cap to move the sealing member.

7. The endoscope according to claim 2, wherein the sealing of the RFID tag storing member by the sealing member is released when the waterproof cap is completely mounted on the connector.

8. A waterproof cap of an endoscope detachably attached to a connector of the endoscope including an RFID tag storing member, an opening and closing member that is capable of opening and closing an opening of the RFID tag storing member, and a moving mechanism configured to move the opening and closing member, the waterproof cap comprising an operating member configured to operate the moving mechanism with an operation of attaching or detaching the waterproof cap to and from the connector.

* * * * *